(12) United States Patent
DeLuca et al.

(10) Patent No.: US 7,648,974 B1
(45) Date of Patent: Jan. 19, 2010

(54) 19-NOR-VITAMIN D ANALOGS WITH 3,2-DIHYDROFURAN RING

(75) Inventors: Hector F. DeLuca, Deerfield, WI (US); Agnieszka Glebocka, Madison, WI (US); Katarzyna Sokolowska, Lomza (PL); Rafal R. Sicinski, Warsaw (PL); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/171,108

(22) Filed: Jul. 10, 2008

(51) Int. Cl.
*A61K 31/59* (2006.01)
*C07C 401/00* (2006.01)
*C07D 317/00* (2006.01)

(52) U.S. Cl. .................. 514/167; 549/456; 549/492; 552/653

(58) Field of Classification Search .............. 552/653; 514/167; 549/462, 429
See application file for complete search history.

(56) References Cited

U.S. PATENT DOCUMENTS

| 5,063,221 A | 11/1991 | Nishii et al. |
|---|---|---|
| 5,086,191 A | 2/1992 | DeLuca et al. |
| 5,536,713 A | 7/1996 | DeLuca et al. |
| 5,545,633 A | 8/1996 | Bretting |
| 5,843,928 A | 12/1998 | DeLuca et al. |
| 5,929,056 A | 7/1999 | Mourino et al. |
| 5,936,133 A | 8/1999 | Deluca et al. |
| 5,945,410 A | 8/1999 | DeLuca et al. |
| 6,382,071 B1 | 5/2002 | Bertani |
| 6,399,797 B1 | 6/2002 | von Daehne et al. |
| 6,566,352 B1 | 5/2003 | DeLuca et al. |
| 6,579,861 B2 | 6/2003 | DeLuca et al. |
| 6,627,622 B2 | 9/2003 | DeLuca et al. |
| 6,929,797 B2 * | 8/2005 | Mazess et al. ......... 424/195.11 |
| 2005/0119242 A1 | 6/2005 | DeLuca et al. |
| 2005/0143358 A1 | 6/2005 | DeLuca et al. |
| 2007/0191316 A1 | 8/2007 | DeLuca et al. |
| 2007/0191317 A1 | 8/2007 | DeLuca et al. |
| 2007/0249567 A1 | 10/2007 | DeLuca et al. |
| 2007/0254857 A1 | 11/2007 | DeLuca et al. |
| 2007/0270391 A1 | 11/2007 | DeLuca et al. |

OTHER PUBLICATIONS

Popeijus, H.E et al. (One page abstract, International Journal of Obesity (2008) 32, 1076-1082, published online on Apr. 22, 2008).*

Argao, EA et al. (abstract of Pediatr. Res., 1992, February;31(2):146-50).*

(Continued)

*Primary Examiner*—Sabiha Qazi
(74) *Attorney, Agent, or Firm*—Andrus, Sceales, Starke & Sawall, LLP

(57) ABSTRACT

19-nor-vitamin D analogs having an additional dihydrofuran ring connecting the 3β-oxygen and carbon-2 of the A-ring of the analog, and pharmaceutical uses therefore, are described. These compounds exhibit selective in vitro and in vivo activities, making them therapeutic agents for the treatment or prophylaxis of autoimmune diseases, some types of cancers, metabolic bone diseases, osteomalacia, osteopenia, secondary hyperparathyroidism, psoriasis, or other skin diseases.

103 Claims, 5 Drawing Sheets

OTHER PUBLICATIONS

Colin W. Pouton (European Journal of Pharmaceutical Sciences 11 Suppl. 2 (2000) 593-598).*

Kamycheva et al, "Intakes of Calcium and Vitamin D Predict Body Mass Index in the Population of Northern Norway," The Journal of Nutrition, 2002.

Arunabh et al, "Body Fat Content and 25-Hydroxyvitamin D Levels in Healthy Women," The Journal of Clinical Endocrinology & Metabolism, 88(1): 157-161, 2003.

Baggiolini et al., "Stereocontrolled Total Synthesis of 1α,25-Dihydroxycholecalciferol and 1α,25- Dihydroxyergocalciferol," Journal of Organic Chemistry, 51, pp. 3098-3108, (1986).

Collins et al, "Normal Functional Characteristics of Cultured Human Promyelocytic Leukemia Cells (HL-60) After Induction of Differentiation by Dimethylsulfoxide," The Journal of Experimental Medicine, vol. 149, pp. 969-974, (1979).

Corey et al, "Computer-Assisted Synthetic Analysis. A Rapid Computer Method for the Semiquantitative Assignment of Conformation of Six-Membered Ring Systems. 1. Derivation of a Preliminary Conformational Description of the Six-Membered Ring," The Journal of Organic Chemistry, vol. 45, No. 5, pp. 757-764, (1980).

Darwish et al, "Identification of Transcription Factor That Binds to the Promoter Region of the Human Parathyroid Hormone Gene," Archives of Biochemistry and Biophysics, vol. 365, No. 1, pp. 123-130, (1999).

Inhoffen et al, "Studies in the Vitamin D Series, XXI: Hydrindane Compounds from Vitamin D3," Chemische Berichte, vol. 90, pp. 664-673, (1957).

Kittaka et al., Synlett, vol. 8, pp. 1175, (1980).

Kittaka et al., Journal of Organic Chemistry, vol. 68, pp. 7407, (2003).

Moras et al., Molecular and Cellular Endocrinology, vol. 5, pp. 173, (2000).

Moras et al., Proc. Natl. Acad. Sci. USA, vol. 98, pp. 5491, (2001).

Ostrem et al, "24- and 26-homo-1,25-dihydroxyvitamin D3: Preferential activity in inducing differentiation of human leukemia cells HL-60 in vitro," Proc. Natl. Acad. Sci. USA, vol. 84, pp. 2610-2614, (1987).

Perlman et al, "Novel Synthesis of 19-Nor-Vitamin D Compounds," Tetrahedron Letters, vol. 32 No. 52, pp. 7663-7666, (1991).

Perlman et al, "1α,25-Dihydroxy-19-Nor-Vitamin D3. A Novel Vitamin D-Related Compound with Potential Therapeutic Activity," Tetrahedron Letters, vol. 31 No. 13, pp. 1823-1824, (1990).

Sicinski et al, Journal of Medical Chemistry, vol. 50, pp. 6154, (2007).

* cited by examiner

19-NOR-VITAMIN D ANALOGS WITH 3,2-DIHYDROFURAN RING

BACKGROUND OF THE INVENTION

This invention relates to vitamin D compounds, and more particularly to 3,2-dihydrofuran-19-nor-vitamin D analogs and their pharmaceutical uses.

The natural hormone, $1\alpha,25$-dihydroxyvitamin $D_3$ and its analog in ergosterol series, i.e. $1\alpha,25$-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

In 1990, a new class of vitamin D analogs was discovered, i.e. the so called 19-nor-vitamin D compounds, characterized by the replacement of the ring A exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, with very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Letters 31, 1823 (1990); Perlman et al., Tetrahedron Letters 32, 7663 (1991), and DeLuca et al., U.S. Pat. No. 5,086,191). A few years later, analogs of $1\alpha,25$-dihydroxy-19-norvitamin $D_3$ substituted at 2-position with hydroxy or alkoxy groups (DeLuca et al., U.S. Pat. No. 5,536,713) were synthesized. Other 2-substituted analogs of $1\alpha,25$-dihydroxy-19-nor-vitamin $D_3$ have also been synthesized, e.g. compounds substituted at 2-position with 2-alkyl groups (DeLuca et al U.S. Pat. No. 5,945,410), and with 2-alkylidene groups (DeLuca et al U.S. Pat. No. 5,843,928). It has been established that they exhibit interesting and selective activity profiles. All these studies indicate that binding sites in vitamin D receptors can accommodate different substituents at C-2 in the synthesized vitamin D analogs.

17-ene vitamin D compounds as well as vitamin D compounds having a double bond in the side chain thereof are also known, and have been proposed for various pharmacological uses. Bone diseases such as osteoporosis, skin disorders such as psoriasis, cancers such as leukemia and cosmetic conditions such as wrinkles are just some of the applications proposed for such compounds. 17-ene compounds are described in U.S. Pat. Nos. 5,545,633; 5,929,056 and 6,399,797 while 2-alkylidene compounds having a side chain with a double bond therein are described in, for example, U.S. Pat. No. 5,843,928.

19-nor vitamin D compounds substituted at the carbon-2 position of ring A with an alkyl group such as methyl, or an alkylidene group such as methylene, and having a side chain lacking one or more of the standard vitamin $D_3$ substitutents, are also known, and have been proposed for various pharmacological uses. For example, numerous $2\alpha$-methyl-19,26,27-trinor analogs are described in published U.S. Application No. 2007/028704 and in published U.S. Application No. 2007/0270391, and numerous 2-methylene-19,26,27-trinor analogs are described in published U.S. Application No. 2007/0249567. In addition, $2\alpha$-methyl-19-nor-(20S)-$1\alpha$-hydroxy-bishomopregnacalciferol is described in published U.S. Application No. 2007/0254857, and numerous 2-methylene-19,26-dinor vitamin D analogs are described in published U.S. Application No. 2007/0191317 and in published U.S. Application No. 2007/0191316.

19-nor-vitamin D analogs which are characterized by the presence of a methylene substituent at carbon 2 (C-2), a hydroxyl group at carbon 1 (C-1), and a shortened side chain attached to carbon 20 (C-20) have also been synthesized and tested. $1\alpha$-hydroxy-2-methylene-19-nor-pregnacalciferol is described in U.S. Pat. No. 6,566,352 while $1\alpha$-hydroxy-2-methylene-19-nor-homopregnacalciferol is described in U.S. Pat. Nos. 6,579,861 and $1\alpha$-hydroxy-2-methylene-19-nor-bishomopregnacalciferol is described in U.S. Pat. No. 6,627,622. Their biological activities make these compounds excellent candidates for a variety of pharmaceutical uses, as set forth in the above patents and published patent applications.

In a continuing effort to explore the 19-nor class of pharmacologically important vitamin D compounds, analogs which are characterized by the transposition of the ring A exocyclic methylene group from carbon 10 (C-10) to carbon 2 (C-2), i.e. 2-methylene-19-nor-vitamin D compounds have been recently synthesized and tested (Sicinski et al., J. Med. Chem., 41, 4662 (1998); Sicinski et al., Steroids 67, 247 (2002); DeLuca et al., U.S. Pat. Nos. 5,843,928, 5,936,133 and 6,382,071). Molecular mechanics studies, performed on these analogs, showed that a change of ring-A conformation can be expected resulting in the "flattening" of the cyclohexanediol ring. From molecular mechanics calculations and NMR studies their A-ring conformational equilibrium was established to be ca. 6:4 in favor of the conformer that has an equatorial $1\alpha$-OH. Introduction of the 2-methylene group into 19-nor-vitamin D carbon skeleton changes the character of its ($1\alpha$- and $3\beta$-) A-ring hydroxyls; they are both now in the allylic positions, similar to the $1\alpha$-hydroxyl group (crucial for biological activity) in the molecule of the natural hormone, $1\alpha,25$-$(OH)_2D_3$. It was found that $1\alpha,25$-dihydroxy-2-methylene-19-norvitamin D analogs are characterized by significant biological potency, enhanced dramatically in compounds with an "unnatural" (20S)-configuration.

Very recently, 2-ethylidene analogs of $1\alpha,25$-dihydroxy-19-norvitamin $D_3$ have been synthesized. It turned out that such modification of the ring A results in significant biological potency of compounds, especially enhanced in the E-geometrical isomers, Sicinski et al., J. Med. Chem., 45, 3366 (2002). Interestingly, it has been established that E-isomers have A-ring conformational equilibrium considerably shifted to one particular chair form, that possessing $1\alpha$-hydroxyl in an equatorial orientation. Also, the analogs which are characterized by the presence of substituted propylidene moiety at C-2 have also been synthesized and preliminary biological tests indicated strong and selective (intestinal) calcemic activity of the E-geometrical isomers.

A-ring conformational equilibrium in vitamin D compounds has attracted considerable research interest for more than 30 years. Development of NMR spectroscopy and force field calculation methods made it possible to establish, or even predict, the proportion of equilibrating $\alpha$- and $\beta$-chair A-ring forms. Parallel to these studies another, closely related problem has been discussed in the literature, namely the correlation of A-ring conformation with biological activities of vitamin D compounds. As early as in 1974 it was proposed [Okamura et al., Proc. Natl. Acad. Sci. USA, 71, 4194 (1974)]

that equatorial orientation of 1α-hydroxy group (i.e., the β-chair form) is necessary for the calcium regulation ability. Recently, Moras reported the crystal structures of hVDR ligand binding domain (LBD) bound to the natural hormone [Moras et al, Moll. Cell, 5, 173 (2000)] and the ligands with unnatural configuration at C-20, [Moras et al, Proc. Natl. Acad. Sci. USA, 98, 5491 (2001)] and it became clear that vitamin D receptor binds (at least in the crystalline state) to vitamin D analogs having their A-rings in β-chair conformation. It seemed, therefore, interesting to synthesize a vitamin D analog that could only assume the opposite α-chair conformation of its ring A, and as a consequence, possesses 1α-hydroxy group in the axial orientation.

As a continuation of the search for biologically active 2-alkylidene-19-norvitamin D compounds, analogs which are characterized by the presence of an additional ring and "flattening bond" system [Corey et al, J. Org. Chem., 45, 757 (1980)] have also been synthesized and tested. Such 19-nor-vitamin D compounds seemed interesting targets because structural constrains of their molecules would prevent their ring A from flipping over to the alternative β-chair form, effectively "freezing" the A-ring c-chair conformation.

SUMMARY OF THE INVENTION

The present invention is directed toward 3,2-dihydrofuran-19-nor-vitamin D analogs, their biological activity, and various pharmaceutical uses for these compounds.

A class of vitamin D compounds not known heretofore are the vitamin D isomers having the A-ring exocyclic methylene moiety at C-10 removed and possessing an additional fused dihydrofuran ring connecting 3 P-oxygen and C-2. Structurally these novel analogs are characterized by the general formula I shown below:

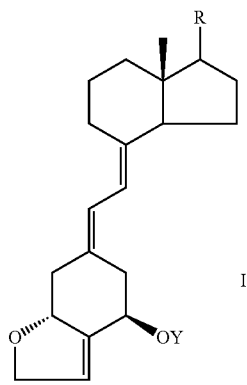

where Y is selected from the group consisting of hydrogen and a hydroxy-protecting group, and where the group R represents any of the typical side chains known for vitamin D type compounds. Thus, R may be an alkyl, hydrogen, hydroxyalkyl or fluoroalkyl group, or R may represent a side chain of the formula:

where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

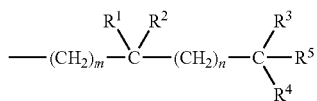

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^5$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

The wavy line to the carbon 20 indicates that carbon 20 may have either the R or S configuration.

Specific important examples of side chains with natural 20R-configuration are the structures represented by formulas (a), b), (c), (d) and (e) below. i.e. the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e).

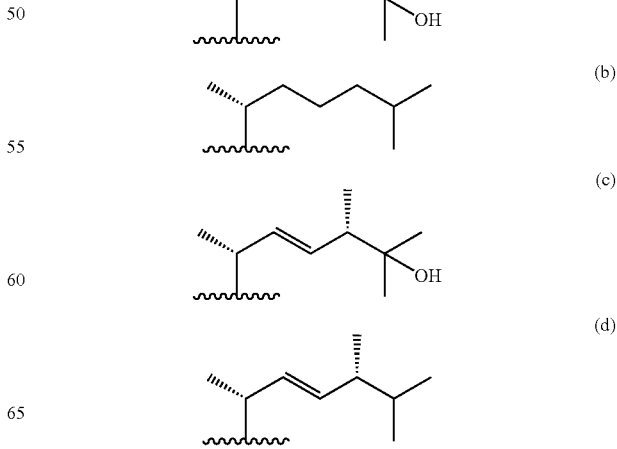

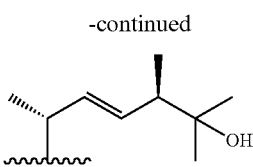
(e)

The preferred analog of formula I is 3,2-dihydrofuran-1α,25-dihydroxy-19-nor-vitamin $D_3$ (hereinafter referred to as "B-REV5") which has the following formula Ia:

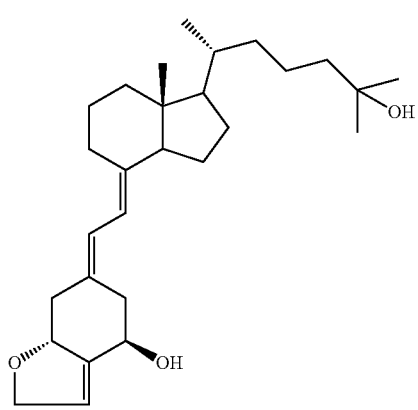
Ia

The above compounds I, and particularly Ia, exhibit a desired, and highly advantageous, pattern of biological activity. This compound has markedly reduced in vitro activities. The VDR binding affinity of B-REV5 is approximately 4 orders of magnitude lower than the native hormone. The potency of B-REV to promote HL60 cell differentiation is 3 logs less than calcitriol. A similar reduction in potency is observed for the in vitro transcription assay conducted in bone cells. Importantly, in vivo this compound exhibits biological activities in bone and intestine that are of only slightly lower potency than 1,25-(OH)$_2$ $D_3$. This in vitro and in vivo disparity can be explained by metabolic conversion to a more active compound only observable in the whole animal system. It is likely that this compound might serve as a slow-release drug or be used as a local-acting drug coupled with an appropriate delivery method. Such compound might be a useful agent for all therapeutic targets of vitamin D analogs, such as autoimmune diseases, some types of cancer, secondary hyperparathyroidism, psoriasis or other skin diseases, or bone diseases.

One or more of the compounds may be present in a pharmaceutical composition to treat or prevent the above-noted diseases and disorders in an amount from about 0.01 µg/gm to about 1000 µg/gm of the composition, preferably from about 0.1 µg/gm to about 500 µg/gm of the composition, and may be administered topically, transdermally, orally, rectally, nasally, sublingually, or parenterally in dosages of from about 0.01 µg/day to about 1000 µg/day, preferably from about 0.1 µg/day to about 500 µg/day.

BRIEF DESCRIPTION OF THE DRAWINGS

FIG. 1 is a graph illustrating the relative activity of B-REV5 and 1,25-(OH)$_2$$D_3$ to compete for binding with [$^3$H]-1,25-(OH)$_2$-$D_3$ to the full-length recombinant rat vitamin D receptor;

FIG. 2 is a graph illustrating the percent HL-60 cell differentiation as a function of the concentration of B-REV5 and 1,25-(OH)$_2$$D_3$;

FIG. 3 is a graph illustrating the in vitro transcription activity of 1,25-(OH)$_2$$D_3$ as compared to B-REV5;

FIG. 4 is a bar graph illustrating the bone calcium mobilization activity of 1,25-(OH)$_2$$D_3$ as compared to B-REV5, and FIG. 5 is a bar graph illustrating the intestinal calcium transport activity of 1,25-(OH)$_2$$D_3$ as compared to B-REV5.

DETAILED DESCRIPTION OF THE INVENTION

Figure 1:
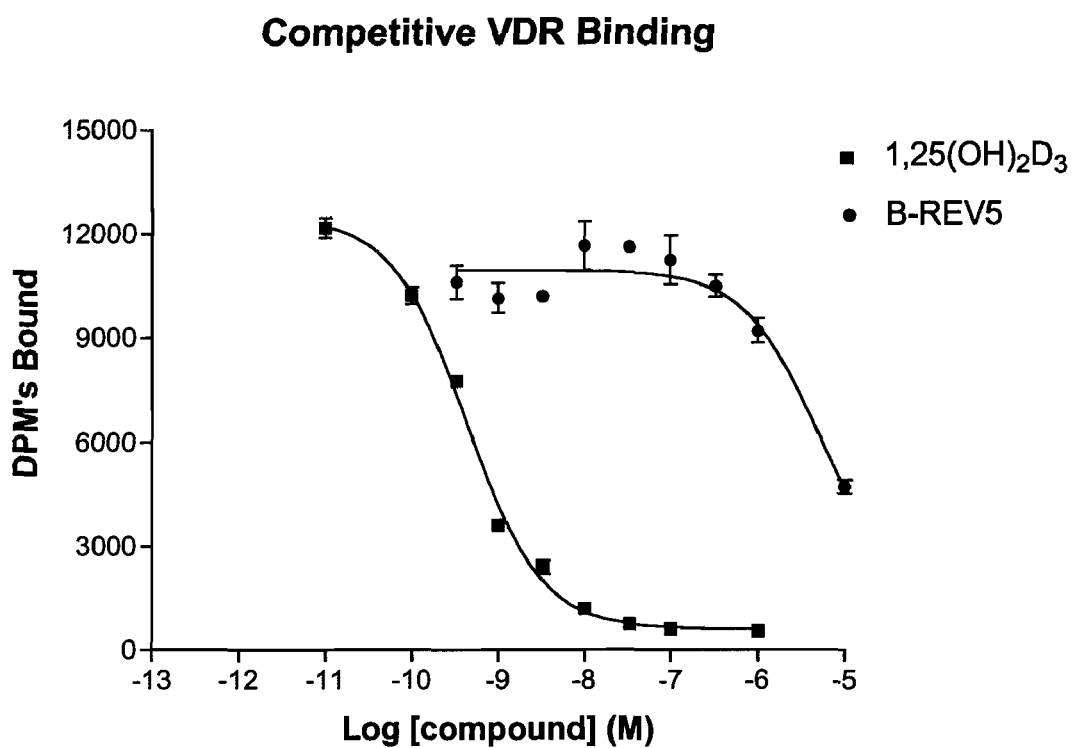
FIGS. 1-5 illustrate various biological activities of 3,2-dihydrofuran-1α,25-dihydroxy-19-nor-vitamin $D_3$ analog 10, referred to as "B-REV5," as compared to the native hormone 1α,25-dihydroxyvitamin $D_3$, hereinafter "1,25(OH)$_2$ $D_3$."

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

The preparation of 19-nor-vitamin D compounds of the basic structures I and II can be accomplished by a common general method, i.e. the Julia olefination involving a coupling of an unsaturated sulfone IV, easily prepared from a bicyclic Windaus-Grundmann type ketone III, with the bicyclic ketone V:

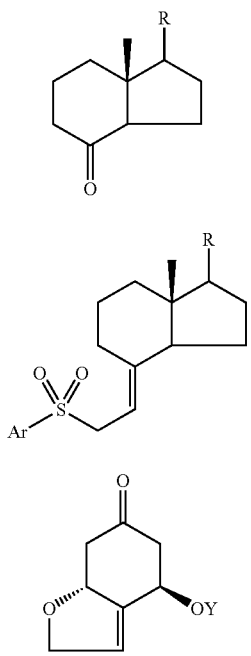

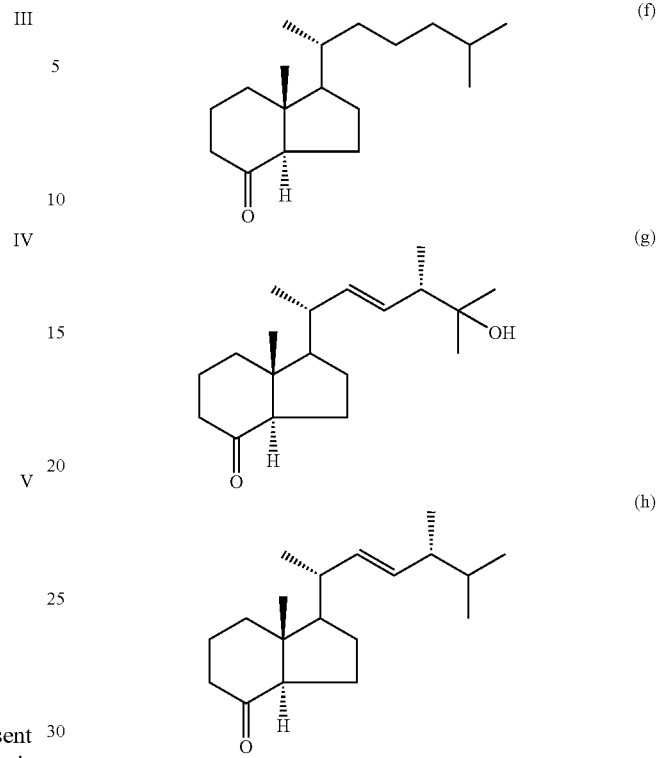

In the structures III, IV and V groups Y and R represent groups defined above whereas Ar represents phenyl, substituted phenyl (preferably phenylthiazoline group) and other aromatic groups that can be suitable for the Julia olefination process, it being also understood that any functionalities in Ar that might be sensitive, or that interfere with the condensation reaction, should be avoided. The process shown above represents an application of the convergent synthesis concept, which has been applied effectively for the preparation of vitamin D compounds (e.g. Kittaka et al, Synlett, 8, 1175 (2003), and J. Org. Chem., 68, 7407 (2003).

Hydrindanones of the general structure III are known, or can be prepared by known methods. Specific important examples of such known bicyclic ketones are the structures with the side chains (a), (b), (c) and (d) described above, i.e. 25-hydroxy Grundmann's ketone (e) [Baggiolini et al., J. Org. Chem., 51, 3098 (1986)]; Grundmann's ketone (f) [Inhoffen et al., Chem. Ber. 90, 664 (1957)]; 25-hydroxy Windaus ketone (g) [Baggiolini et al., J. Org. Chem., 51, 3098 (1986)] and Windaus ketone (h) [Windaus et al., Ann., 524, 297 (1936)]:

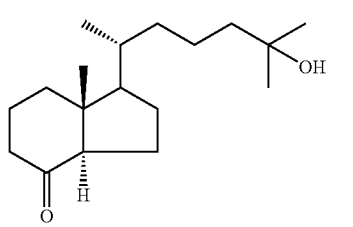

For the preparation of the required bicyclic ketones of general structure V, a new synthetic route has been developed starting from cyclohexanedione derivative 1 that was obtained from commercial (1R,3R,4S,5R)-(−)-quinic acid as described previously [Sicinski et al., J. Med. Chem., 45, 3366 (2002)]. Process of transformation of the starting diketone 1 into the desired A-ring synthon is shown on the SCHEME I. Due to a considerable difference in the steric hindrance between the two carbonyl groups, it was possible to achieve selective protection of one of them providing mono thioacetal 2 in 53% yield. The following Wittig reaction with an ylide, generated from methyltriphenylphosphonium bromide and n-BuLi, proved to be more efficient (84%) and resulted in the methylenation of the remaining carbonyl carbon. Then, one of the two secondary hydroxy groups of the obtained product 3 was selectively deprotected and the alcohol 4, formed in 55% yield, was then subjected to Williamson reaction. Thus, an anion of 4 generated with sodium hydride reacted with allyl bromide to form an allylic ether 5 in 69% yield. Ring closing methatesis of compound 5 was performed in a presence of commercially available Grubb's II generation catalyst 6. The expected tricyclic compound 7 was obtained in 81% yield. Deprotection of the carbonyl group in 7 was achieved by its treatment with thallium(III) trifluoroacetate. The desired A-ring fragment 8, formed in 70% yield, was then subjected to modified Julia olefination with the anion generated from thiazoline sulphone 9 [prepared from the corresponding Grundmann ketone according to the known procedure, Sicinski et al., J. Med. Chem., 50, 6154 (2007)] accepted for publication) and lithium bis(trimethylsilyl)amide. Removal of the silyl protecting groups in the obtained 19-norvitamins gave the expected mixture of two 19-norvitamin D analogs 10 and 11 which were purified and separated by straight- and reversed-phase HPLC. Analysis of their $^1$H NMR spectra confirmed that ring A in these compounds, due to the presence of an exocyclic double bond being a part of additional five-membered ring, is prevented from flipping and held in the single chair conformation.

Several other 19-nor-vitamin D compounds may be synthesized by the method disclosed herein using the A-ring synthon 8 and the appropriate C,D-fragments derived from the Windaus-Grundmann ketones having the desired side chain structure.

This invention is described by the following illustrative examples. In these examples specific products identified by Arabic numerals (e.g. 1, 2, 3, etc) refer to the specific structures so identified in the preceding description and in the SCHEME I.

EXAMPLES

Chemistry. Melting points (uncorrected) were determined on a Thomas-Hoover capillary melting-point apparatus. Ultraviolet (UV) absorption spectra were recorded with a Perkin-Elmer Lambda 3B UV-VIS spectrophotometer in ethanol. $^1$H nuclear magnetic resonance (NMR) spectra were recorded at 200, 400 and 500 MHz with a Bruker Instruments DMX-400 and DMX-500 Avance console spectrometers in deteriochloroform. $^{13}$C nuclear magnetic resonance (NMR) spectra were recorded at 125 MHz with a Varian Unity plus 200 spectrometer, and Bruker Instruments DMX-500 Avance console spectrometer in deuteriochloroform. Chemical shifts ($\delta$) are reported downfield from internal Me$_4$Si ($\delta$0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example I

Preparation of 19-Norvitamin D$_3$ Analogues 10 and 11

Referring to SCHEME I the starting cyclohexanedione 1 was obtained from commercial (−)-quinic acid according to the described procedure, Sicinski et al., J. Med. Chem. 45, 3366 (2002).

(a) Selective Protection of Carbonyl Group in Diketone 1

(2R,6R)-2,6-Bis [(tert-butyldimethylsilyl)oxy]-4,4-ethylenedithio-cyclohexanone (2). To a stirred solution of 1,2-ethanedithiol (0.25 mL, 3.0 mmol) and Zn(OTf)$_2$ (646 mg, 1.78 mmol) in anhydrous methylene chloride (7.2 mL) was transferred a solution of 1 (964 mg, 2.24 mmol) in anhydrous methylene chloride (9.6 mL) at 0° C. under argon. The mixture was stirred at 0° C. for 1 h, and at room temperature for 1.5 h and then it was poured into brine and extracted with ethyl acetate. The extract was washed with saturated NaHCO$_3$, water, 5% HCl, again water, dried (MgSO$_4$) and evaporated. The residue was purified by column chromatography on silica. Elution with hexane/ethyl acetate (96:4) afforded an oily ketone 2 (729 mg, 53%). 2: $[\alpha]^{20}_D$ −52° (c 0.1, CHCl$_3$); $^1$H NMR (200 MHz, CDCl$_3$) $\delta$ 0.078 and 0.085 (2×6H, 2×s, 4×SiCH$_3$), 0.92 (2×9H, s, 2×Si-t-Bu), 2.35 (2H, ddd, J=14.0, 7.4, 1.5 Hz, 3$\alpha$- and 5$\beta$-H), 2.57 (2H, ddd, J=14.0, 4.6, 1.5 Hz, 3$\beta$- and 5$\alpha$-H), 3.23-3.38 (4H, m, S—CH$_2$CH$_2$—S), 4.63 (2H, dd, J=7.4, 4.6 Hz, 2$\beta$- and 6$\alpha$-H).

(b) Wittig Reaction of Ketone 2

(1R,3R)-1,3-Bis[(tert-butyldimethylsilyl)oxy]-5,5-ethylenedithio-2-methylenecyclohexane (3). To the methyltriphenylphosphonium bromide (59 mg, 0.167 mmol) in anhydrous THF (0.8 mL) was added at 0° C. n-BuLi (1.6 M in cyclohexane, 105 µL, 0.167 mmol) under argon with stirring. The orange-red mixture was cooled to −78° C. and siphoned to a stirred solution of ketone 2 (30 mg, 0.067 mmol) in anhydrous THF (0.5 mL). The mixture was stirred at −78° C. for 2 h, and the reaction was quenched by the addition of brine containing 1% HCl. Saturated NaHCO$_3$ (3 mL), water (3 mL), diethyl ether (3 mL) and ethyl acetate (6 mL) were added and the mixture was vigorously stirred at room temperature. After 16 h the layers were separated, organic phase was washed with brine, dried (MgSO$_4$), and evaporated. The residue was purified by column chromatography on silica. Elution with hexane/ethyl acetate (99:1) gave an oily compound 3 (25 mg, 84%). 3: $[\alpha]^{20}_D$ −24° (c 0.1, CHCl$_3$); $^1$H NMR (200 MHz, CDCl$_3$) $\delta$ 0.056 and 0.079 (2×6H, 2×s, 4×SiCH$_3$), 0.92 (2×9H, s, 2×Si-t-Bu), 2.07 (2H, br dd, J=13.2, 7.1 Hz, 4$\alpha$- and 6$\beta$-H), 2.39 (2H, ddd, J=13.2, 4.0, 1.0 Hz, 4$\beta$- and 6$\alpha$-H), 3.07-3.30 (4H, m, S—CH$_2$CH$_2$—S), 4.59 (2H, dd, J=7.1, 4.0, Hz, 1$\alpha$- and 3$\beta$-H), 4.94 (2H, s, =CH$_2$).

(c) Selective Deprotection of Hydroxyl Group in Compound 3

(3R)-3-[(tert-Butyldimethylsilyl)oxy]-5,5-ethylenedithio-2-methylenecyclohexanol (4). To a solution of compound 3 (93 mg, 208 µmol) in anhydrous THF (7.8 mL) was added tetrabutylammonium fluoride (1M in THF; 208 µL, 208 µmol) and the mixture was stirred for 18 h. It was then poured into brine and extracted with ethyl acetate. Organic phase was washed with brine, dried (MgSO$_4$), and evaporated. The residue was purified by column chromatography on silica. Elution with hexane/ethyl acetate (96:4) gave an oily alcohol 4 (38 mg, 55%). 4: $[\alpha]^{20}_D$ −44.6° (c 0.15, CDCl$_3$); $^1$H NMR (200 MHz, CDCl$_3$) $\delta$ 0.082 and 0.100 (2×3H, 2×s, 2×SiCH$_3$), 0.92 (9H, s, Si-t-Bu), 2.14 (2H, m, 4$\beta$- and 6$\alpha$-H), 2.41 (2H, m, 4$\alpha$- and 6$\beta$-H), 3.32 (4H, s, S—CH$_2$CH$_2$—S), 4.60 (2H, m, 1$\beta$-i 3$\alpha$-H), 5.03 and 5.06 (2H, 2×s, =CH$_2$).

(d) Williamson Reaction of Compound 4 with Allyl Bromide (1R,3R)-1-Allyloxy-3-[(tert-Butyldimethylsilyl)oxy]-5,5-ethylenedithio-2-methylenecyclohexane (5). Sodium hydride (60% suspension in oil; 8.5 mg, 0.213 mmol) was washed with anhydrous hexane (1 mL) under argon, 18-crown-6 (8.5 mg, 32 µmol) was added, and then a solution of cyclohexanol 4 (22 mg, 66 µmol) in anhydrous DMF (0.63 mL) was siphoned to the reaction flask. After 5 min of stirring allyl bromide (87.8 mg, 89 µl, 0.726 mmol) was added. The mixture was stirred at room temperature for 1.5 h, water was added and the mixture was extracted with ethyl acetate. Organic phase was separated, washed with water, dried (MgSO$_4$), and evaporated. The residue was purified by column chromatography on silica. Elution with hexane/ethyl acetate (99:1) gave an oily compound 5 (17 mg, 69%). 5: $[\alpha]^{20}_D$ −45° (c 0.6, CDCl$_3$); $^1$H NMR (200 MHz, CDCl$_3$) $\delta$ 0.079 and 0.088 (2×3H, 2×s, 2×SiCH$_3$), 0.93 (9H, s, Si-t-Bu), 2.00 (1H, dd, J=12.7, 9.3 Hz, 413-H), 2.37 (2H, m, 6$\alpha$- and 6$\beta$-H), 2.41 (1H, dd, J=12.7, 4.6 Hz, 4$\alpha$-H), 3.22-3.35 (4H, narr m, S—CH$_2$CH$_2$—S), 3.86 (2H, m, OCH$_2$CH=CH$_2$), 4.16 (1H, t, J=4.4 Hz, 1$\beta$-H), 4.57 (1H, m, 3$\alpha$-H), 4.97 [(1H, br s, one of C(2)=CH$_2$], 5.15 [1H, m, C(2')H=CH$_{trans}$], 5.17

[(1H, br s, one of C(2)=CH$_2$], 5.35 [1H, br ddd, J=17.0, 4.0, 2.0 Hz, C(2')H=CH$_{cis}$], 5.93 (1H, br m, CH$_2$—CH=).

(e) Ring Closing Methatesis of Compound 5

(4R,7aR)-4-[(tert-Butyldimethylsilyl)oxy]-6,6-etylenodithio-2,4,5,6,7,7a-hexahydro-benzofuran (7). To a stirred solution of compound 5 (12 mg, 0.032 mmol) in anhydrous toluene (8 mL) at 80° C. Grubb's II generation catalyst 6 (2.7 mg, 3 µmol) was added. The mixture was for 40 min, and then it was cooled to room temperature. The mixture was applied on Waters silica Sep-Pak to remove the catalyst and eluted with anhydrous toluene. The residue was purified by column chromatography on silica. Elution with hexane/ethyl acetate (99:1) gave an oily compound 7 (9 mg, 81%). 7: $[\alpha]^{20}_D$ −29.5° (c 0.4, CDCl$_3$); $^1$H NMR (500 MHz, CDCl$_3$) δ 0.069 and 0.084 (3H and 3H, 2×s, 2×SiCH$_3$), 0.91 (9H, s, Si-t-Bu), 1.77 (1H, dd, J=12.5, 10.5 Hz, 7α-H), 2.27 (1H, dd, J=14.0, 2.5 Hz, 5α-H), 2.41 (1H, dt, J=14.0, 2.5 Hz, 5β-H), 2.63 (1H, ddd, J=12.5, 5.5, 2.5, 7'-H), 3.25 (4H, br m, S—CH$_2$CH$_2$—S), 4.62 (1H, ddd, J=13.0, 4.5, 1.5 Hz, 2α-H), 4.67 (1H, ddd, J=13.0, 3.0, 1.5 Hz, 2β-H), 4.72 (1H, t, J=2.5 Hz, 4α-H), 5.09 (2H, br m, w/2=22 Hz, 7aβ-H), 5.54 (1H, m, 3-H); MS (ESI) exact mass calculated for C$_{16}$H$_{28}$O$_2$S$_2$Si$_2$Na 367.1 (M$^+$+Na). Found 367.2.

(f) Deprotection of Carbonyl Group in Compound 7

(4R,7aR)-4-[(tert-Butyldimethylsilyl)oxy]-4,5,7,7a-tetrahydro-2H-benzofuran-6-one (8). Thallium trifluoroacetate (39 mg, 60 mmol) was added at room temperature to a solution of 7 (20 mg, 58 mmol) in anhydrous THF (1 mL). After stirring for 40 min saturated Na$_2$SO$_3$ was added, the mixture was poured into water and extracted with ethyl acetate. Organic phase was washed with water, dried (MgSO$_4$), and evaporated to give a colorless residue which was purified by column chromatography on silica. Elution with hexane/ethyl acetate (95:5) gave ketone 8 (6 mg, 38%; 70% based on recovered substrate). The column was then washed with hexane/ethyl acetate (9:1) to afford the unreacted thioacetal 7 (9 mg). 8: $[\alpha]^{24}_D$ −92° (c 0.28, CHCl$_3$); $^1$H NMR (400 MHz, CDCl$_3$) δ 0.034 and 0.073 (3H and 3H, each s, 2×SiCH$_3$), 0.843 [9H, s, Si-t-Bu], 2.42 (1H, br d, J=14.3 Hz, 5β-H), 2.44 (1H, dd, J=13.4, 10.0 Hz, 7α-H), 2.51 (1H, dd, J=14.3, 3.4 Hz, 5α-H), 3.00 (1H, ddd, J=13.4, 6.5, 1.6 Hz, 7β-H), 4.77 (2H, d, J=4.5 Hz, 2α- and 2β-H), 4.92 (1H, narr m, 4α-H), 5.17 (1H, br m w/2=19 Hz, 7aβ-H), 5.76 (1H, br s, 3-H); $^{13}$C NMR (125 MHz) δ −5.1 (Si—CH$_3$), −4.9 (Si—CH$_3$), 18.0 [C(CH$_3$)$_3$], 25.7 [C(CH$_3$)$_3$], 50.5 and 50.8 (C$_5$ and C$_7$), 65.7 (C$_{7a}$), 75.9 (C$_2$), 81.7 (C$_4$), 119.7 (C$_3$), 141.1 (C$_{3a}$), 206.5 (C$_6$).

(g) Julia Coupling of Ketone 8 and Sulfone 9

1α,25-Dihydroxy- and 25-hydroxy-19-norvitamin D$_3$ analogues (10 and 11). To a solution of sulfone 9 (30.0 mg, 48 µmol) in dry THF (200 µL) was added LiHMDS (1 M in THF, 48 µL, 48 µmol) at −78° C. under argon. The solution turned deep red. The mixture was stirred at −78° C. for 20 min and a solution of the ketone 8 (5.4 mg, 20 µmol) in THF (100+80 µL) was added. The stirring was continued at −78° C. for 1.5 h, and the reaction mixture was allowed to warm to −10° C. during ca. 1.5 h. Then it was poured into saturated NH$_4$Cl and extracted with ether. The extract was washed with brine, dried (Na$_2$SO$_4$) and evaporated. The yellow oily residue was applied on silica Sep-Pak, eluted with hexane/ethyl acetate (98:2), concentrated under vacuum, dissolved in anhydrous methanol (1 mL) and treated with (+)-10-camphorosulfonic acid (15 mg, 64.5 µmol). The solution was stirred at room temperature under argon for 19 h, poured into brine, and extracted with ethyl acetate. The extract was washed with diluted NaHCO$_3$ and brine, dried (Na$_2$SO$_4$) and evaporated. The residue was purified by HPLC (9.4 mm×25 cm Zorbax-Sil column, 4 mL/min) using hexane/2-propanol (87:13) solvent system. Isomeric 19-norvitamins 10 (B-REV5) (1.4 mg, 17%) and 11 (A-REV5) (0.5 mg, 6%) were collected at R$_V$ 30 mL and R$_V$ 35 mL, respectively. Final purification and separation of both isomers was achieved by reversed-phase HPLC (9.4 mm×25 cm Zorbax-ODS column, 4 mL/min) using methanol/water (95:5) solvent system: 25-hydroxyvitamin D analogue 11 was collected at R$_V$ 19 mL and isomeric 1α,25-dihydroxyvitamin D analogue 10 at R$_V$ 23 mL.

10 (B-REV5): UV (in EtOH) λ$_{max}$ 245.5, 253.0, 262.0 nm; $^1$H NMR (400 MHz, CDCl$_3$) δ 0.549 (3H, s, 18-H$_3$), 0.939 (3H, d, J=6.3 Hz, 21-H$_3$), 1.219 (6H, s, 26- and 27-H$_3$), 2.81 (2H, m, 4α-H overlapped with 9β-H), 3.09 (1H, d, J=14.0 Hz, 10α-H), 4.69 (2H, narr m, CH$_2$—O), 4.76 (1H, br s, 1β-H), 4.90 (1H, m, w/2=19 Hz, 3α-H), 5.71 (1H, narr m, O—CH$_2$—HC=C), 5.85 and 6.48 (1H and 1H, each d, J=11.2 Hz, 7- and 6-H.

11 (A-REV5): UV (in EtOH) λ$_{max}$ 245.5, 253.0, 262.5 nm; $^1$H NMR (600 MHz, CDCl$_3$) δ 0.551 (3H, s, 18-H$_3$), 0.940 (3H, d, J=6.3 Hz, 21-H$_3$), 1.22 (6H, s, 26- and 27-H$_3$), 1.85 (1H, t, J~11.5 Hz, 10α-H), 2.47 (2H, narr m, 4α- and 4β-H), 2.82 (1H, br d, J=13.0 Hz, 9β-H), 3.36 (1H, dd, J=11.9, 5.9 Hz, 10β-H), 4.70 (3H, narr m, 3α-H overlapped with CH$_2$—O), 4.82 (1H, m, w/2=25 Hz, 1β-H), 5.70 (1H, br s, O—CH$_2$—HC=C), 5.90 and 6.36 (1H and 1H, each d, J=11.2 Hz, 7- and 6-H); HRMS (ESI) exact mass calcd for C$_{28}$H$_{44}$O$_3$Na (M+Na)$^+$ 451.3188, measured 451.3197.

SCHEME I

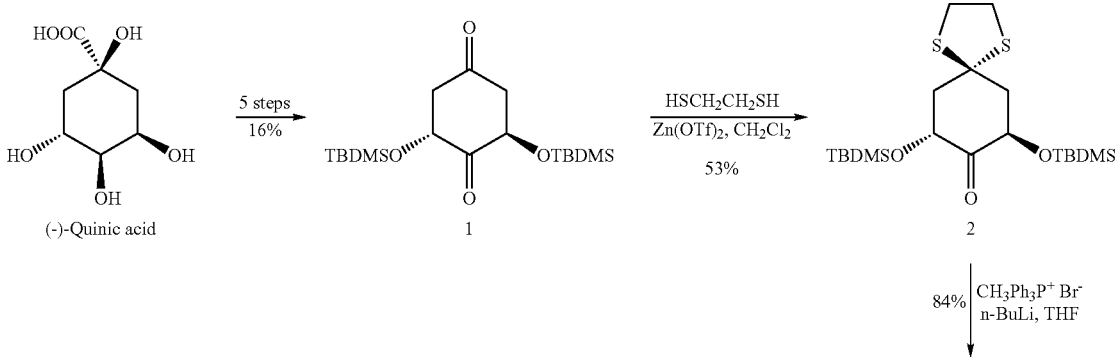

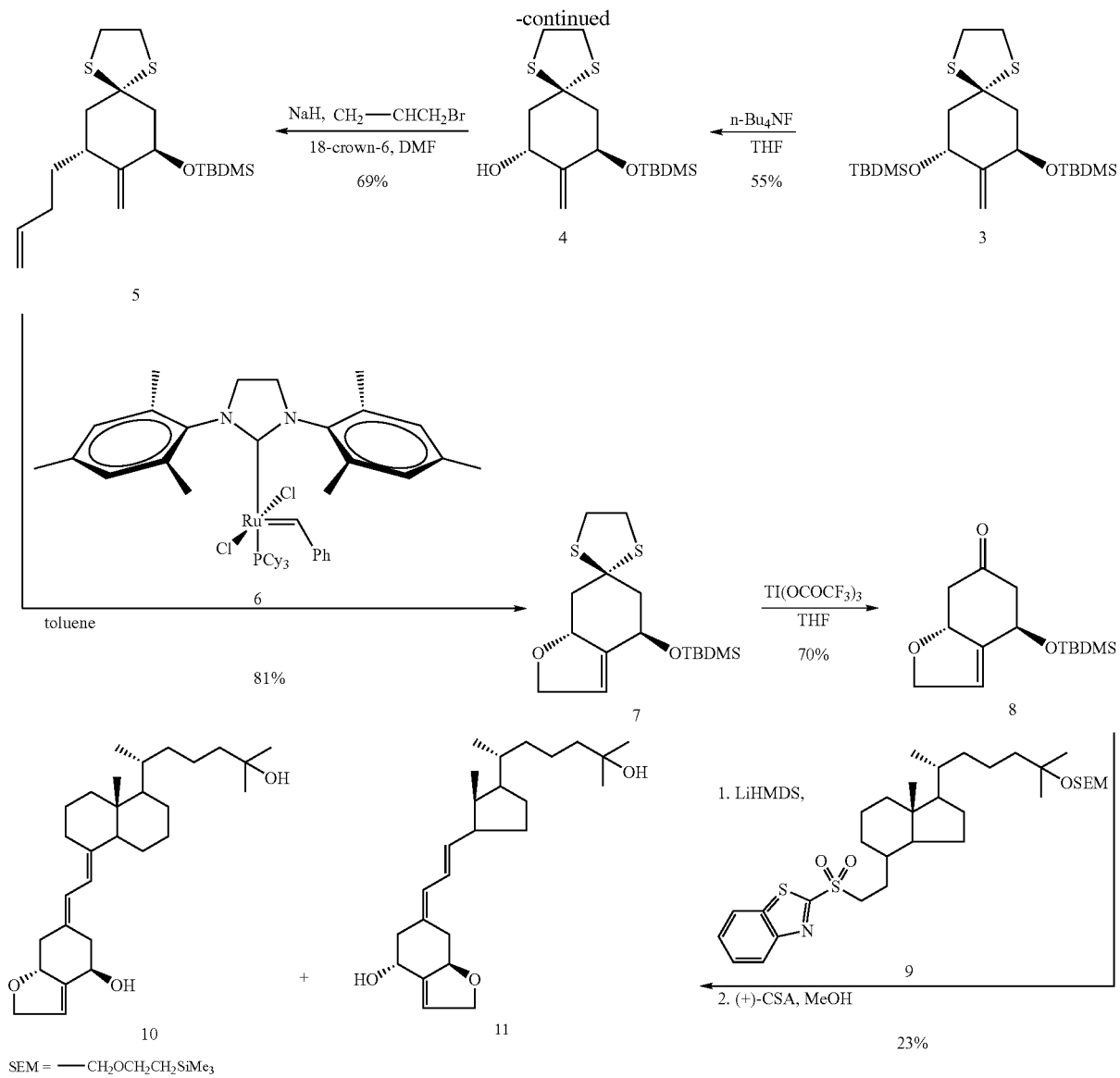

Biological Activity of 3,2-Dihydrofuran-1α,25-Dihydroxy-19-nor Vitamin $D_3$ Compound (Analog 10, B-REV5)

The introduction of a fused dihydrofuran ring connecting 3β-oxygen and carbon-2 (analog 10, B-REV5) diminished binding to the full length recombinant rat vitamin D receptor, as compared to 1α,25-dihydroxyvitamin $D_3$ by about 1 log or 10-fold (FIG. 1). Despite a reduced receptor binding activity in vitro, this compound in vivo had significant intestinal calcium transport activity with no activity in bone mobilization. Thus, B-REV5 is an analog with highly unique selective biological activity.

Figure 5:
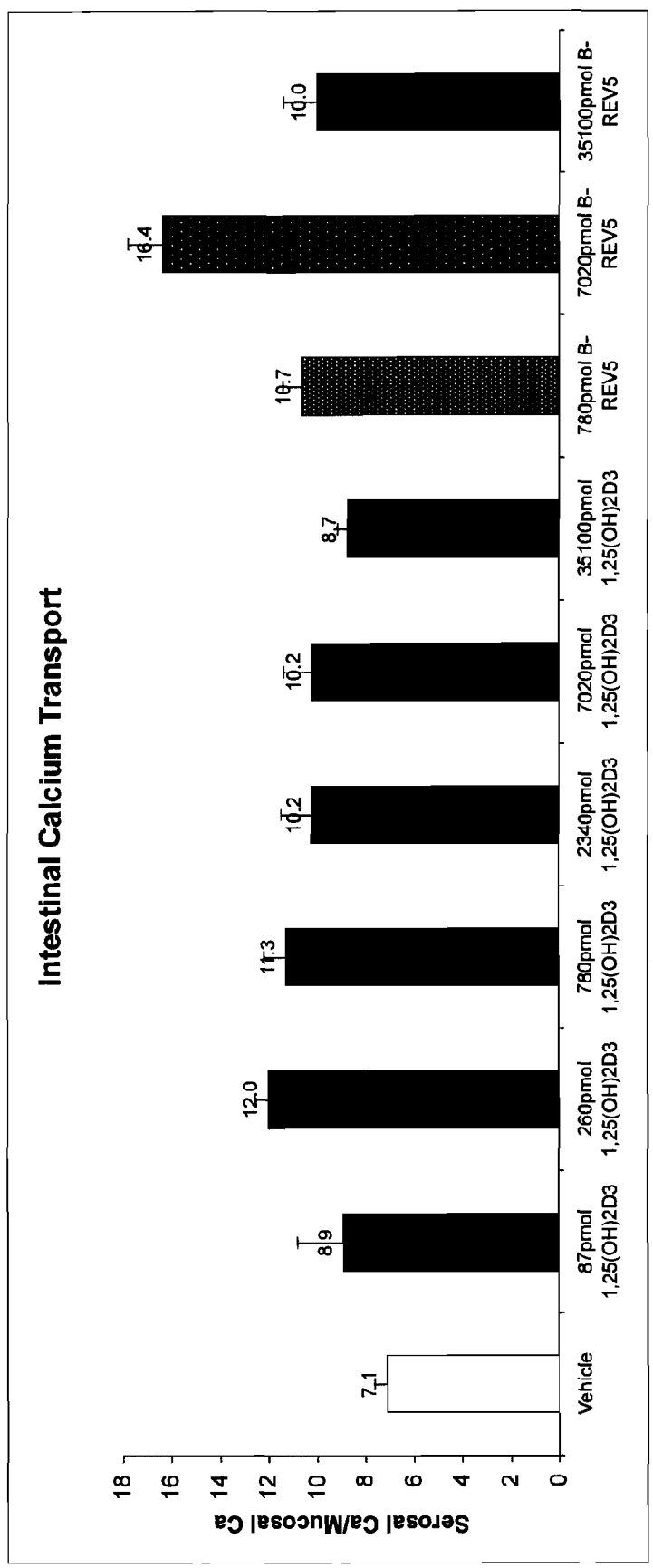

FIG. 5 shows that B-REV5 has very significant ability to increase intestinal calcium transport activity in vivo. It clearly has about the same potency in vivo as compared to that of 1,25-dihydroxyvitamin $D_3$ (1,25-$(OH)_2D_3$), the natural hormone, in stimulating intestinal calcium transport.

Figure 4:
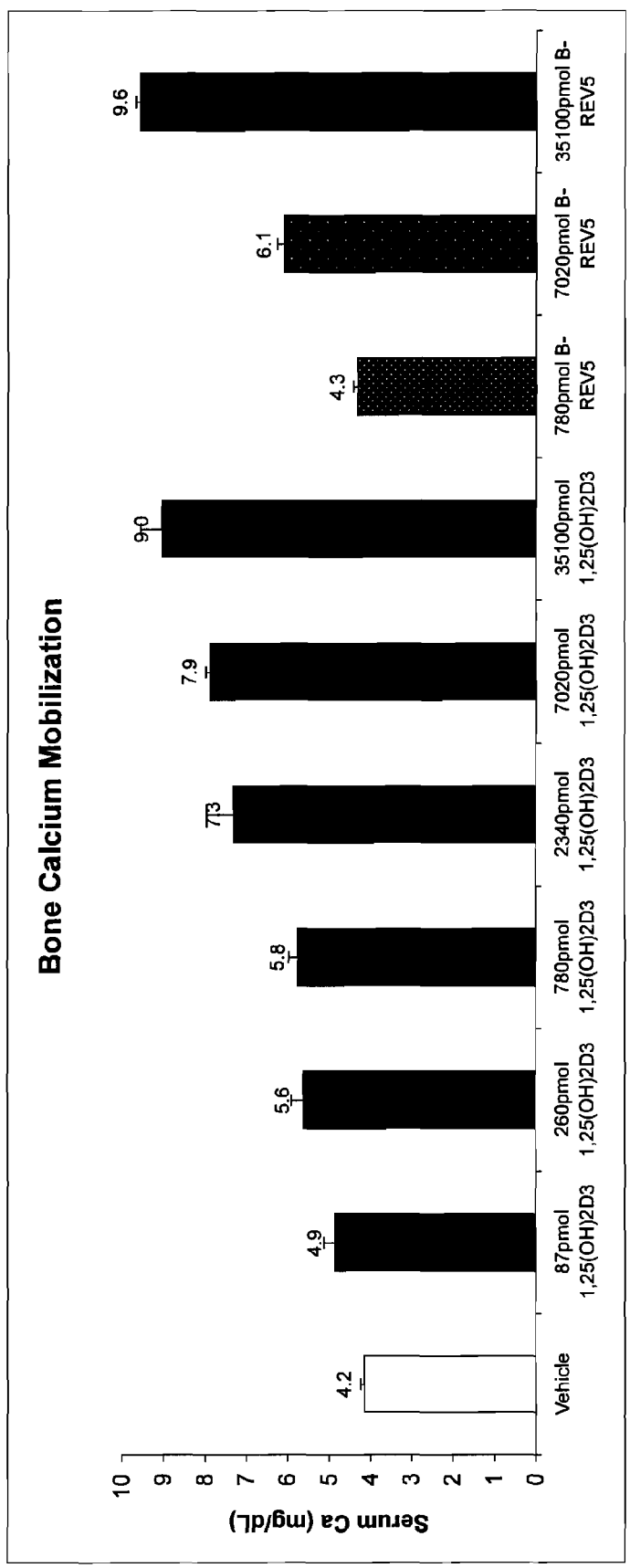

FIG. 4 demonstrates that B-REV5 also has very significant bone calcium mobilization activity, as compared to 1,25-$(OH)_2D_3$. B-REV5 demonstrated only slightly less bone calcium mobilization activity at the doses as compared to of 1,25-$(OH)_2D_3$. Thus, B-REV5 clearly has significant potency in mobilizing calcium from bone as compared to 1,25-$(OH)_2 D_3$, at the recommended doses.

FIGS. 4 and 5 thus illustrate that B-REV5 may be characterized as having substantially high intestinal calcium transport activity, as well as substantially high bone calcium mobilization activity, i.e. as having significant calcemic activity. The preferential activity on bone calcium mobilizing activity allows the in vivo administration of this compound for the treatment and prophylaxis of metabolic bone diseases. Because of its preferential activity on bone, this compound would be a preferred therapeutic agent for the treatment and prophylaxis of diseases such as osteoporosis, especially low bone turnover osteoporosis, steroid induce osteoporosis, senile osteoporosis or postmenopausal osteoporosis, as well as osteomalacia, osteopenia and renal osteodystrophy.

Figure 2:
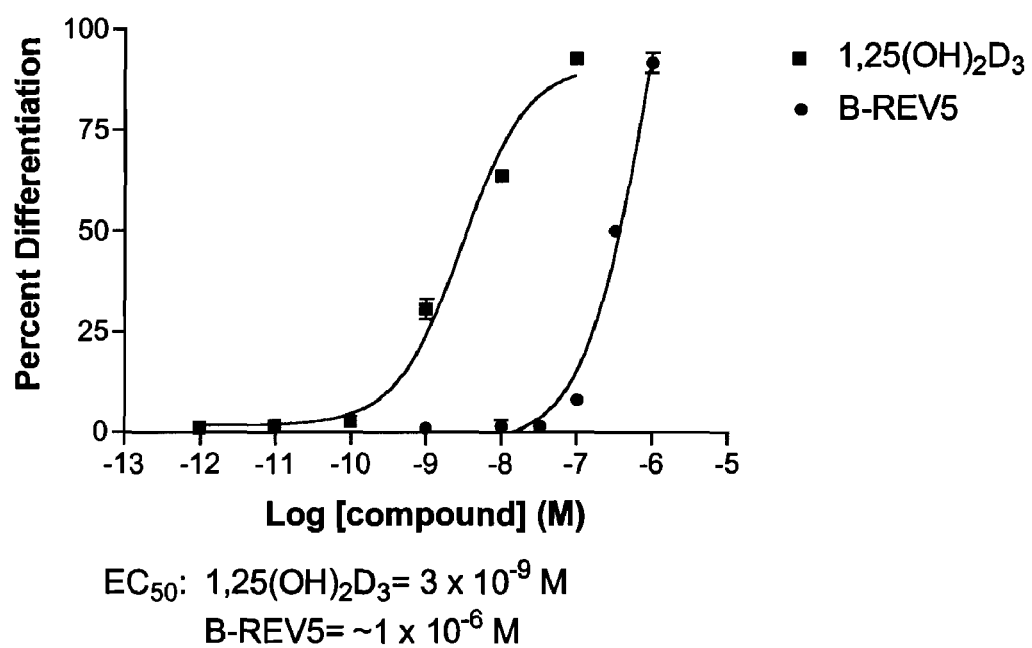

FIG. 2 illustrates that B-REV5 is considerably less active than 1,25-(OH)$_2$D$_3$ on HL-60 cell differentiation. The data show it is about 1,000 times less active than 1,25(OH)$_2$D$_3$.

Figure 3:
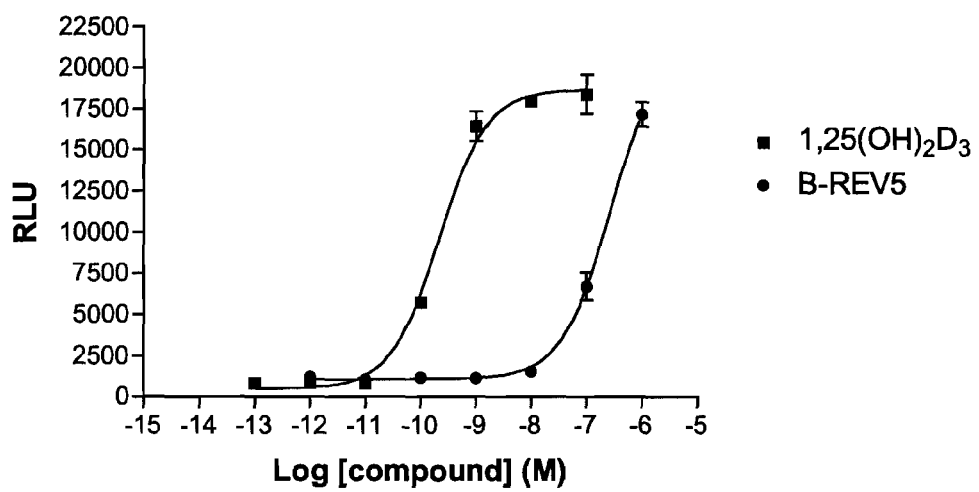

FIG. 3 illustrates that the compound B-REV5 has much less transcriptional activity (about 1000 times less potent) than 1α,25-dihydroxyvitamin D$_3$ in bone cells.

Although not as potent as 1α,25-(OH)$_2$D$_3$, B-REV5 still has cell differentiation activity, and thus the activity of B-REV5 on cell differentiation suggests that B-REV5 may be an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

FIG. 3 illustrates that in bone cells the compound B-REV5 has some ability to increase transcription of the 24-hydroxylase gene. This result, together with the cell differentiation activity of FIG. 2, suggests that B-REV5 will be very effective in psoriasis because it has direct cellular activity in causing cell differentiation, gene transcription, and in suppressing cell growth. These data also indicate that B-REV5 may have significant activity as an anti-cancer agent, especially against leukemia, colon cancer, breast cancer, skin cancer and prostate cancer.

The activity of B-REV5 on HL-60 differentiation suggests it will be active in suppressing growth of parathyroid glands and in the suppression of the preproparathyroid gene. It is undesirable to raise serum calcium to supraphysiologic levels when suppressing the preproparathyroid hormone gene (Darwish & DeLuca, Arch. Biochem. Biophys. 365, 123-130, 1999) and parathyroid gland proliferation. These analogs having relatively low bone calcium mobilization activity while active on cell differentiation are expected to be useful as a therapy for suppression of secondary hyperparathyroidism of renal osteodystrophy.

Experimental Methods

Vitamin D Receptor Binding
Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25-(OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25-(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

VDR binding, HL60 cell differentiation, and transcription activity. B-REV5 ($K_i=8\times10^{-7}M$) has much lower ability than the natural hormone 1α,25-dihydroxyvitamin $D_3$ ($K_i=7\times10^{-11}M$) in its ability to compete with [$^3$H]-1,25(OH)$_2$D$_3$ for binding to the full-length recombinant rat vitamin D receptor (FIG. 1). B-REV5 is about 4 logs, or 40 times, less potent than 1,25-(OH)$_2$D$_3$ in its affinity for the VDR. B-REV5 ($EC_{50}=1\times10^{-6}M$) is also considerably lower in its ability to promote HL60 differentiation as compared to 1α,25-dihydroxyvitamin $D_3$ ($EC_{50}=3\times10^{-9}M$) (See FIG. 2). The ability of the vitamin B-REV5 to induce differentiation of human promyelocyte HL-60 cells into monocytes is about 1,000 times less potent than the natural hormone (FIG. 2). Also, compound B-REV5 ($EC_{50}=3\times10^{-7}M$) has much lower transcriptional activity in bone cells than 1α,25-dihydroxyvitamin $D_3$ ($EC_{50}=2.0\times10^{-10}M$) (see FIG. 3). Thus, B-REV5 has weak transcriptional activity, indicated in the 24-hydroxylase (CYP-24) promoter driving luciferase reporter gene system, and is about 1,000 times less potent than 1,25-(OH)$_2$D$_3$ in increasing transcription of the 24-hydroxylase gene (see FIG. 3).

Calcium mobilization from bone in vitamin D-deficient animals. Using vitamin D-deficient mice on a low calcium diet (0.02%), the activities of B-REV5 and 1,25-(OH)$_2$D$_3$ in bone were tested. As expected, the native hormone (1,25-(OH)$_2$D$_3$) increased serum calcium levels at all the dosages tested (FIG. 4).

The study reported in FIG. 4 shows that B-REV5 has relatively high activity in mobilizing calcium from bone. B-REV5 is only slightly less potent than 1α,25-(OH)$_2$D$_3$ as the administration of 7,020 pmol/day of B-REV5 for 4 consecutive days resulted in a serum calcium value of 6.1 mg/dL whereas the native hormone 1,25-(OH)$_2$D$_3$ had a value of 7.9 mg/dL at 7,020 pmol/day.

Intestinal calcium transport was evaluated in the same group of animals using the everted gut sac method (FIG. 5). The study reported in FIG. 5 shows B-REV5 has relatively significant intestinal calcium transport activity which is similar to 1,25-(OH)$_2$D$_3$. Administration of 780 pmol/day of B-REV5 for 4 consecutive days resulted in almost the same activity as 1,25-(OH)$_2$D$_3$ at 780 pmol/day.

These results show that the compound B-REV5 promotes intestinal calcium transport and bone calcium mobilization. Thus, it may be concluded that B-REV5 has similar intestinal calcium transport activity and is only slightly less potent in bone calcium mobilization activity to that of 1,25-(OH)$_2$D$_3$ at the recommended doses.

These results illustrate that B-REV5 is an excellent candidate for numerous human therapies as described herein, and that it may be particularly useful in a number of circumstances such as suppression of secondary hyperparathyroidism of renal osteodystrophy, autoimmune diseases, cancer, numerous types of skin conditions, and psoriasis, metabolic bone diseases, osteomalcia and osteopenia. B-REV5 is an excellent candidate for treating psoriasis because: (1) it has VDR binding, transcription activity and cellular differentiation activity; (2) it has low hypercalcemic liability, unlike 1,25-(OH)$_2$D$_3$; and (3) it is easily synthesized. Since B-REV5 has binding activity to the vitamin D receptor, but has relatively low ability to raise blood serum calcium, it may also be particularly useful for the treatment of secondary hyperparathyroidism of renal osteodystrophy.

The compounds of the invention of formula I, and particularly B-REV5 of formula Ia, are characterized as having significant calcemic activity. Their preferential activity on bone calcium mobilizing activity allows the in vivo administration of these compounds for the treatment and prophylaxis of metabolic bone diseases. Because of their preferential activity on bone, these compounds would be preferred therapeutic agents for the treatment and prophylaxis of diseases such as osteoporosis, especially low bone turnover osteoporosis, steroid induced osteoporosis, senile osteoporosis or postmenopausal osteoporosis, as well as osteomalacia, osteopenia and renal osteodystrophy.

These data also indicate that the compound B-REV5 of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound B-REV5 of the invention.

The compounds of the invention of formula I, and particularly B-REV5 of formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I, particularly B-REV5, may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly B-REV5, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 μg to 1000 μg per day of the compounds I, particularly B-REV5, preferably from about 0.01 μg to about 500 μg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly B-REV5, as defined by the above formula I and Ia as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually, or parenterally in dosages of from about 0.01 μg/day to about 1000 μg/day, and preferably from about 0.1 μg/day to about 500 μg/day.

The compounds I, particularly B-REV5, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly B-REV5, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

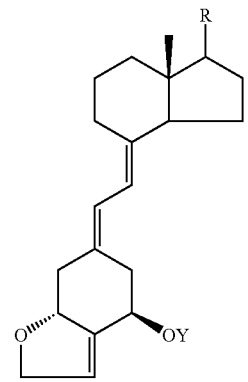

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —$CH_2OY$, —C≡CY and —CH=CHY, where the double bond in the side chain may have the cis or trans geometry, and where Y is selected from hydrogen, methyl, —$COR^5$ and a radical of the structure:

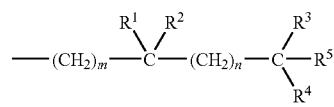

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

2. The compound of claim 1 wherein Y is hydrogen.

3. A pharmaceutical composition containing an effective amount of at least one compound as claimed in claim 1 together with a pharmaceutically acceptable excipient.

4. The pharmaceutical composition of claim 3 wherein said effective amount comprises from about 0.01 μg to about 1000 μg per gram of composition.

5. The pharmaceutical composition of claim 3 wherein said effective amount comprises from about 0.1 μg to about 500 μg per gram of composition.

6. 3,2-dihydrofuran-1α,25-dihydroxy-19-nor-vitamin D$_3$ having the formula:

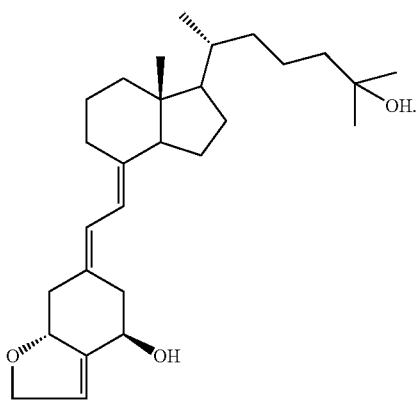

Ia

7. A pharmaceutical composition containing an effective amount of 3,2-dihydrofuran-1α,25-dihydroxy-19-nor-vitamin D$_3$ together with a pharmaceutically acceptable excipient.

8. The pharmaceutical composition of claim 7 wherein said effective amount comprises from about 0.01 μg to about 1000 μg per gram of composition.

9. The pharmaceutical composition of claim 7 wherein said effective amount comprises from about 0.1 μg to about 500 μg per gram of composition.

10. A method of treating psoriasis comprising administering to a subject with psoriasis an effective amount of a compound having the formula:

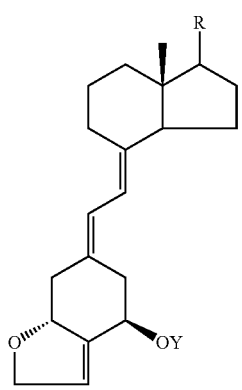

I where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

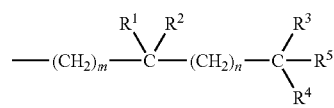

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

11. The method of claim 10 wherein the compound is administered orally.

12. The method of claim 10 wherein the compound is administered parenterally.

13. The method of claim 10 wherein the compound is administered transdermally.

14. The method of claim 10 wherein the compound is administered topically.

15. The method of claim 10 wherein the compound is administered rectally.

16. The method of claim 10 wherein the compound is administered nasally.

17. The method of claim 10 wherein the compound is administered sublingually.

18. The method of claim 10 wherein the compound is administered in a dosage of from about 0.01 μg/day to about 1000 μg/day.

19. The method of claim 10 wherein the compound is 3,2-dihydrofuran-1α,25-dihydroxy-19-nor-vitamin D$_3$ having the formula:

23

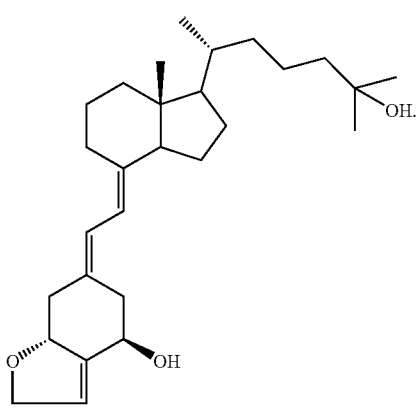

20. A method of treating a disease selected from the group consisting of leukemia, colon cancer, breast cancer, skin cancer or prostate cancer comprising administering to a subject with said disease an effective amount of a compound having the formula:

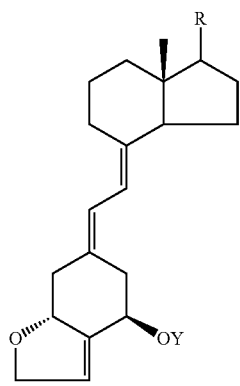

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

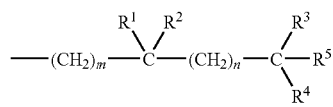

24 where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$— where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

21. The method of claim 20 wherein the compound is administered orally.

22. The method of claim 20 wherein the compound is administered parenterally.

23. The method of claim 20 wherein the compound is administered transdermally.

24. The method of claim 20 wherein the compound is administered rectally.

25. The method of claim 20 wherein the compound is administered nasally.

26. The method of claim 20 wherein the compound is administered sublingually.

27. The method of claim 20 wherein the compound is administered in a dosage of from about 0.01 µg/day to about 1000 µg/day.

28. The method of claim 20 wherein the compound is 3,2-dihydrofuran-1α,25-dihydroxy-19-nor-vitamin D$_3$ having the formula:

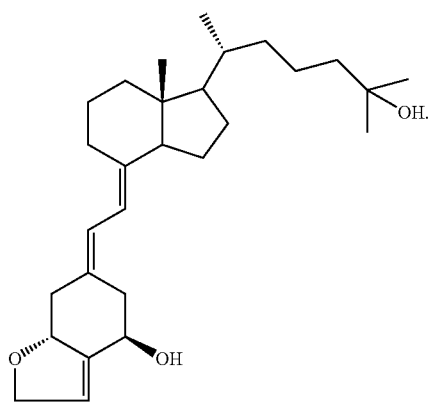

29. A method of treating an autoimmune disease selected from the group consisting of multiple sclerosis, lupus, diabetes mellitus, host versus graft rejection, and rejection of organ transplants, comprising administering to a subject with said disease an effective amount of a compound having the formula:

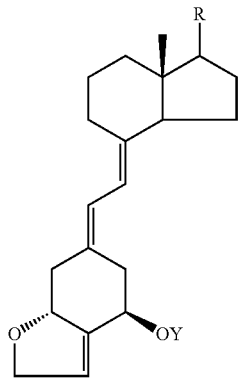

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

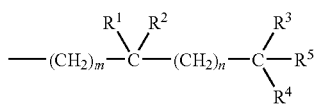

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

30. The method of claim 29 wherein the compound is administered orally.

31. The method of claim 29 wherein the compound is administered parenterally.

32. The method of claim 29 wherein the compound is administered transdermally.

33. The method of claim 29 wherein the compound is administered rectally.

34. The method of claim 29 wherein the compound is administered nasally.

35. The method of claim 29 wherein the compound is administered sublingually.

36. The method of claim 29 wherein the compound is administered in a dosage of from about 0.01 μg/day to about 1000 μg/day.

37. The method of claim 29 wherein the compound is 3,2-dihydrofuran-1α,25-dihydroxy-19-nor-vitamin D$_3$ having the formula:

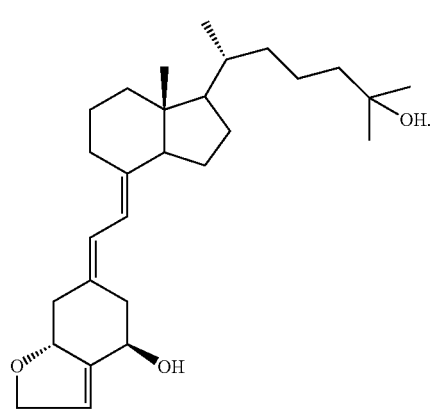

38. A method of treating an inflammatory disease selected from the group consisting of rheumatoid arthritis, asthma, and inflammatory bowel diseases, comprising administering to a subject with said disease an effective amount of a compound having the formula:

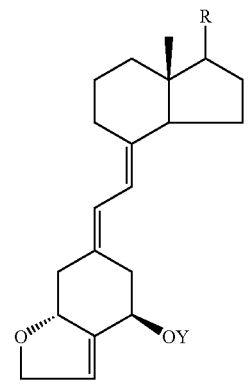

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

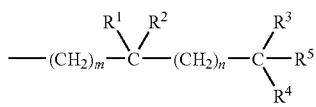

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

39. The method of claim 38 wherein the compound is administered orally.

40. The method of claim 38 wherein the compound is administered parenterally.

41. The method of claim 38 wherein the compound is administered transdermally.

42. The method of claim 38 wherein the compound is administered rectally.

43. The method of claim 38 wherein the compound is administered nasally.

44. The method of claim 38 wherein the compound is administered sublingually.

45. The method of claim 38 wherein the compound is administered in a dosage of from about 0.01 µg/day to about 1000 µg/day.

46. The method of claim 38 wherein the compound 3,2-dihydrofuran-1α,25-dihydroxy-19-nor-vitamin D$_3$ having the formula:

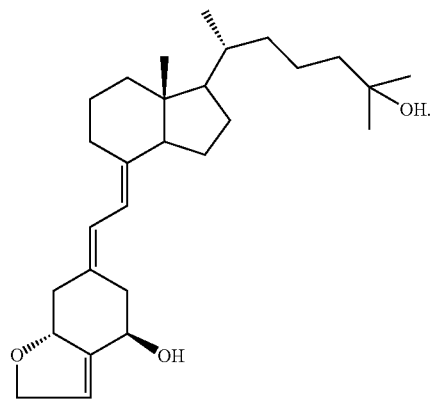

47. A method of treating a skin condition selected from the group consisting of wrinkles, lack of adequate skin firmness, lack of adequate dermal hydration and insufficient sebum secretion which comprises administering to a subject with said skin condition an effective amount of a compound having the formula:

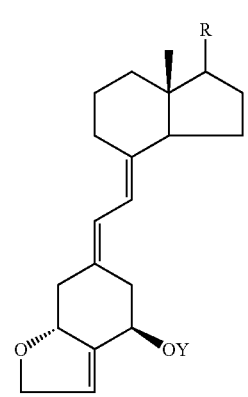

where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

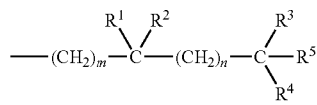

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group $=CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_5$alkyl and wherein any of the CH-groups at positions 20, 22, or 23 in the side chain may be replaced by a nitrogen atom, or where any of the groups —$CH(CH_3)$—, —$(CH_2)_m$—, —$CR_1R_2$— or —$(CH_2)_n$— at positions 20, 22, and 23, respectively, may be replaced by an oxygen or sulfur atom.

48. The method of claim 47 wherein the compound is administered orally.

49. The method of claim 47 wherein the compound is administered parenterally.

50. The method of claim 47 wherein the compound is administered transdermally.

51. The method of claim 47 wherein the compound is administered topically.

52. The method of claim 47 wherein the compound is administered rectally.

53. The method of claim 47 wherein the compound is administered nasally.

54. The method of claim 47 wherein the compound is administered sublingually.

55. The method of claim 47 wherein the compound is administered in a dosage of from about 0.01 µg/day to about 1000 µg/day.

56. The method of claim 47 wherein the compound is 3,2-dihydrofuran-1α,25-dihydroxy-19-nor-vitamin $D_3$ having the formula:

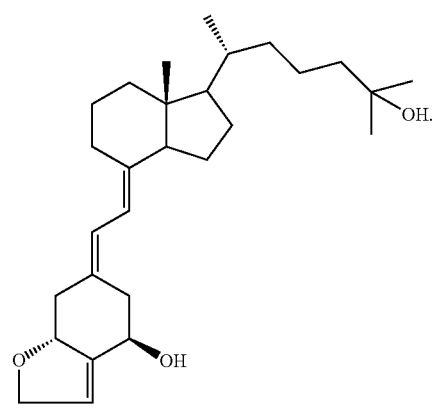

57. A method of treating renal osteodystrophy comprising administering to a subject with renal osteodystrophy an effective amount of a compound having the formula:

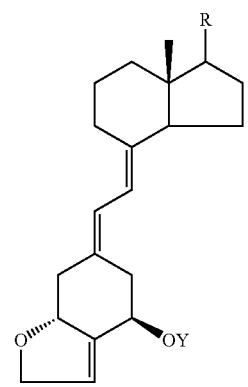

where Y is selected from the group consisting of hydrogen and a hydroxy-protecting group, and where the group R represents an alkyl hydrogen, hydroxyalkyl, or fluoroalkyl group, or R may represent a side chain of the formula:

where Z in the above side chain structure is selected from Y, —OY, —$CH_2OY$, —$C\equiv CY$ and —$CH=CHY$, where the double bond in the side chain may have the cis or trans geometry, and where Y is selected from hydrogen, methyl, —$COR^5$ and a radical of the structure:

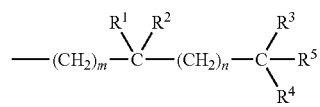

where m and n, independently, represent the integers from 0 to 5, where $R^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

58. The method of claim 57 wherein the compound is administered orally.

59. The method of claim 57 wherein the compound is administered parenterally.

60. The method of claim 57 wherein the compound is administered transdermally.

61. The method of claim 57 wherein the compound is administered rectally.

62. The method of claim 57 wherein the compound is administered nasally.

63. The method of claim 57 wherein the compound is administered sublingually.

64. The method of claim 57 wherein the compound is administered in a dosage of from about 0.01 μg/day to about 1000 μg/day.

65. The method of claim 57 wherein the compound is 3,2-dihydrofuran-1α,25-dihydroxy-19-nor-vitamin D$_3$ having the formula:

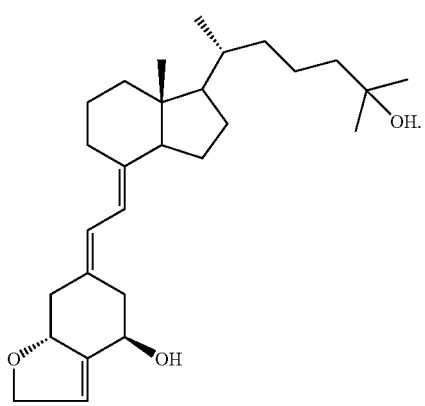

Ia

66. A method of treating obesity of an animal, inhibiting adipocyte differentiation, inhibiting SCD-1 gene transcription, and/or reducing body fat in an animal comprising administering to an animal in need thereof an effective amount of a compound having the formula:

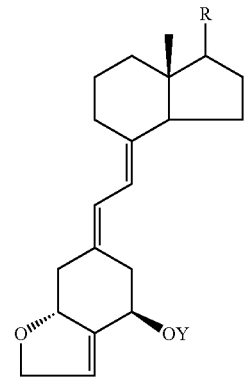

I where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

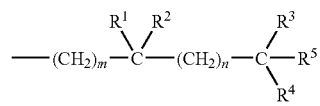

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)—, —CR$_1$R$_2$— or —(CH$_2$)$_n$— at positions 20, 22, and 23, respectively, may be replaced by an oxygen or sulfur atom.

67. The method of claim 66 wherein the compound is administered orally.

68. The method of claim 66 wherein the compound is administered parenterally.

69. The method of claim 66 wherein the compound is administered transdermally.

70. The method of claim 66 wherein the compound is administered rectally.

71. The method of claim 66 wherein the compound is administered nasally.

72. The method of claim 66 wherein the compound is administered sublingually.

73. The method of claim 66 wherein the compound is administered in a dosage of from about 0.01 µg/day to about 1000 µg/day.

74. The method of claim 66 wherein the compound is 3,2-dihydrofuran-1α,25-dihydroxy-19-nor-vitamin $D_3$ having the formula:

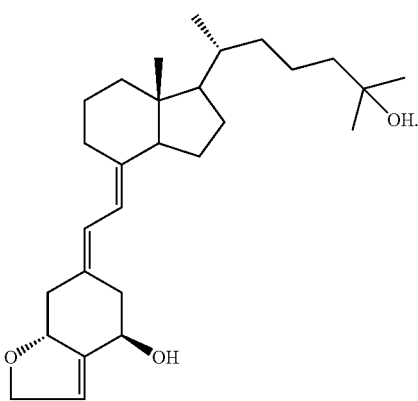

Ia

75. The method of claim 66 wherein the animal is a human.

76. The method of claim 66 wherein the animal is a domestic animal.

77. The method of claim 66 wherein the animal is an agricultural animal.

78. A method of treating a metabolic bone disease comprising administering to a subject with said disease an effective amount of a compound having the formula:

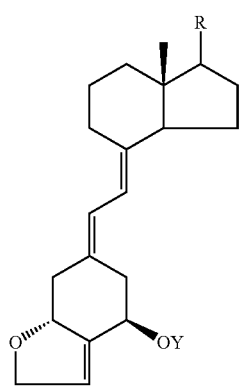

I where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

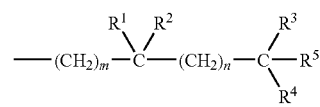

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

79. The method of claim 78 where the disease is senile osteoporosis.

80. The method of claim 78 where the disease is postmenopausal osteoporosis.

81. The method of claim 78 where the disease is steroid-induced osteoporosis.

82. The method of claim 78 where the disease is low bone turnover osteoporosis.

83. The method of claim 78 where the disease is osteomalacia.

84. The method of claim 78 wherein the compound is administered orally.

85. The method of claim 78 wherein the compound is administered parenterally.

86. The method of claim 78 wherein the compound is administered transdermally.

87. The method of claim 78 wherein the compound is administered rectally.

88. The method of claim 78 wherein the compound is administered nasally.

89. The method of claim 78 wherein the compound is administered sublingually.

90. The method of claim 78 wherein the compound is administered in a dosage of from about 0.01 µg/day to about 1000 mg/day.

91. The method of claim 78 wherein the compound is a 3,2-dihydrofuran-1α,25-dihydroxy-19-nor-vitamin D₃ analog having the formula:

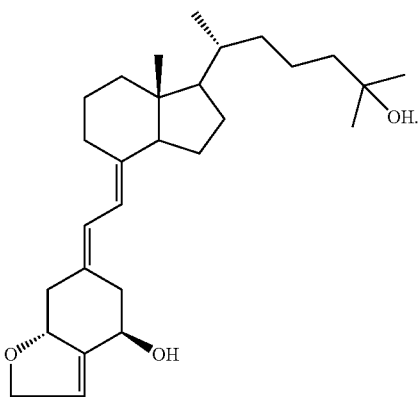

Ia

92. A method of treating osteopenia comprising administering to a subject with osteopenia an effective amount of a compound having the formula:

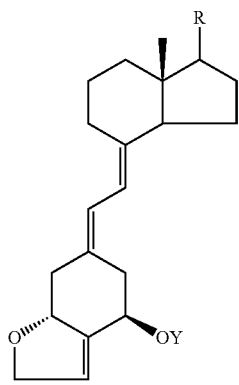

I where Y is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH₂OY, —C≡CY and —CH═CHY, where the double bond in the side chain may have the cis or trans geometry, and where Y is selected from hydrogen, methyl, —COR⁵ and a radical of the structure:

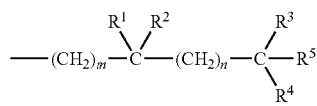

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group $=CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH₃)—, —(CH₂)ₘ—, —CR₁R₂— or —(CH₂)ₙ— at positions 20, 22, and 23, respectively, may be replaced by an oxygen or sulfur atom.

93. The method of claim 92 wherein the compound is administered orally.

94. The method of claim 92 wherein the compound is administered parenterally.

95. The method of claim 92 wherein the compound is administered transdermally.

96. The method of claim 92 wherein the compound is administered rectally.

97. The method of claim 92 wherein the compound is administered nasally.

98. The method of claim 92 wherein the compound is administered sublingually.

99. The method of claim 92 wherein the compound is administered in a dosage of from about 0.01 μg/day to about 1000 mg/day.

100. The method of claim 92 wherein the compound is a 3,2-dihydrofuran-1α,25-dihydroxy-19-norvitamin D₃ analog having the formula:

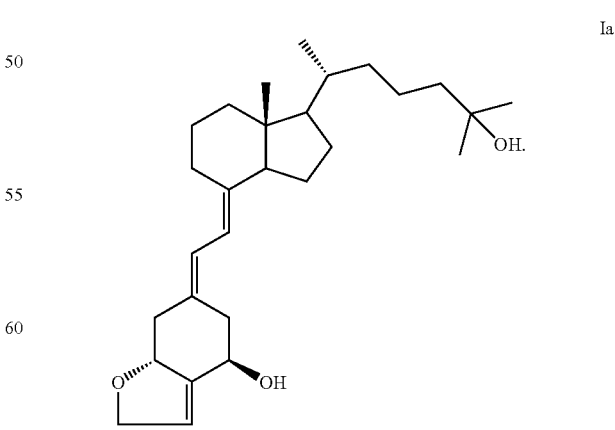

Ia

101. A compound having the formula:
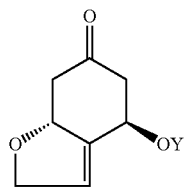
where Y is selected from the group consisting of hydrogen and a hydroxy-protecting group.
102. The compound of claim 101 wherein Y is hydrogen.
103. The compound of claim 101 wherein Y is t-butyldimethylsilyl.
* * * * *